(12) United States Patent
Simionescu

(10) Patent No.: US 10,596,699 B2
(45) Date of Patent: Mar. 24, 2020

(54) PARALLEL MECHANISM MASTICATOR AND CHEWING APPARATUS

(71) Applicant: Petru Aurelian Simionescu, Corpus Christi, TX (US)

(72) Inventor: Petru Aurelian Simionescu, Corpus Christi, TX (US)

(*) Notice: Subject to any disclaimer, the term of this patent is extended or adjusted under 35 U.S.C. 154(b) by 134 days.

(21) Appl. No.: 15/790,844

(22) Filed: Oct. 23, 2017

(65) Prior Publication Data

US 2019/0118376 A1   Apr. 25, 2019

(51) Int. Cl.
*B25J 9/16* (2006.01)
*B23Q 1/54* (2006.01)
*A61C 11/08* (2006.01)
*B23Q 3/18* (2006.01)
*G05B 19/4063* (2006.01)
(Continued)

(52) U.S. Cl.
CPC ............ *B25J 9/1623* (2013.01); *A61C 11/02* (2013.01); *A61C 11/081* (2013.01); *B23Q 1/5437* (2013.01); *B23Q 3/18* (2013.01); *G05B 19/4063* (2013.01); *G09B 23/283* (2013.01); *G05B 2219/50162* (2013.01)

(58) Field of Classification Search
CPC ...... A61C 11/02; A61C 11/081; B25J 9/1623; G09B 23/283; G05B 19/4063; G05B 2219/50162; B23Q 3/18; B23Q 1/5437
USPC .......................................................... 433/69
See application file for complete search history.

(56) References Cited

U.S. PATENT DOCUMENTS 4,330,276 A * 5/1982 Becker ................ A61C 19/045
433/55
4,351,553 A * 9/1982 Rovetta ................ B25J 15/0009
294/106
(Continued)

OTHER PUBLICATIONS

Chiang M.-H. and Lin H.-T. (2011) "Development of a 3D Parallel Mechanism Robot Arm with Three Vertical-Axial Pneumatic Actuators Combined with a Stereo Vision System," Sensors, 11, p. 11476-11494.
(Continued)

*Primary Examiner* — Matthew M Nelson

(57) ABSTRACT

The present invention is concerned with an apparatus for simulating the chewing process for the purpose of testing dental materials and implants and for the purpose of analyzing food samples. The apparatus comprises a frame, a stationary platform connected compliantly to the said frame and a moving platform corresponding to the maxillae and mandible of humans or animals, to which dentures or teeth are affixed. The moving platform is guided and driven in mandibular motion using six rods fitted with spherical joints at both ends. Said ball-jointed rods are attached with one end to the moving platform, and with the other end either to the frame of the apparatus, or to rotary cranks driven synchronously by a motor via a transmission. The rotary cranks together with their motor and transmission are mounted on a carrier which is adjustably attached to the frame of the apparatus. To closely reproduce a desired mandibular motion, the locations of the spherical joints to the frame, the position and orientation of the carrier relative to the frame, and the lengths of the rotary cranks and of the ball-jointed rods are suitably adjusted.

10 Claims, 2 Drawing Sheets

(51) Int. Cl.
*G09B 23/28* (2006.01)
*A61C 11/02* (2006.01)

(56) References Cited

U.S. PATENT DOCUMENTS

| | | | | |
|---|---|---|---|---|
| 4,468,198 A * | 8/1984 | Kataoka | ............... | A61C 19/045 433/54 |
| 5,006,065 A * | 4/1991 | Waysenson | ............ | A61C 11/02 433/54 |
| 5,743,732 A * | 4/1998 | Watson | ................. | A61C 19/04 433/55 |
| 5,865,063 A * | 2/1999 | Sheldon | ............... | B23Q 1/5462 248/653 |
| 6,120,290 A * | 9/2000 | Fukushima | ............ | A61C 11/00 433/69 |
| 6,547,172 B2 * | 4/2003 | Reinders | ................ | G09B 23/28 241/236 |
| 7,124,660 B2 * | 10/2006 | Chiang | .................. | A47B 91/16 74/490.05 |
| 7,172,385 B2 * | 2/2007 | Khajepour | ........... | B25J 17/0266 414/735 |
| 7,204,168 B2 * | 4/2007 | Najafi | ...................... | A61B 8/00 74/471 XY |
| 7,686,529 B1 * | 3/2010 | Le | .......................... | B64G 1/646 403/78 |
| 8,021,149 B2 * | 9/2011 | Gutman | ................. | A61C 11/00 433/229 |
| 8,333,766 B2 * | 12/2012 | Edelhauser | ............ | A61B 17/62 606/55 |

OTHER PUBLICATIONS

Condon J.R. and Ferracane J.L. (1996) "Evaluation of composite wear with a new multi-mode oral wear simulator." Dental Materials, vol. 12(4), p. 218-226.

Cong M., Du J., Liu T., Wen H. and Xu W. (2012) "Design and Simulation Experiment Research of a New Jaw Movement Robot" Proc. of the World Congress on Engineering and Computer Science WCECS 2012, Oct. 24-26, 2012, San Francisco, USA, vol. I, 6 p.

Delong R. and Douglas W.H. (1983) "Development of an artificial oral environment for the testing of dental restoratives: bi-axial force and movement control," Journal of Dental Research, 62(1), p. 32-36.

Raabe D., Harrison A., Ireland A., Alemzadeh K., Sandy J., Dogramadzi S., Melhuish C. and Burgess S. (2012) "Improved single- and multi-contact life-time testing of dental restorative materials using key characteristics of the human masticatory system and a force/position-controlled robotic dental wear simulator" Bioinspiration & Biomimetics, 7(1), 016002 (17p).

Simionescu, P.A. (2017) "A unified approach to the kinematic synthesis of five-link, four-link, and double-wishbone suspension mechanisms with rack-and-pinion steering control", Proceedings of the Institution of Mechanical Engineers, Part D: Journal of Automobile Engineering, 231(10), p. 1374-1387.

Wand L., Sadler J.P. and Breeding L.C. (1998) "A robotic system for testing dental implants," Mechanism and Machine Theory, 33(5), p. 583-597.

* cited by examiner

PARALLEL MECHANISM MASTICATOR AND CHEWING APPARATUS

BACKGROUND OF INVENTION

1. Technical Field

The present invention relates to dentistry including prosthodontics and to food and nutrition sciences, and more particular relates to an apparatus for simulating the chewing process for the purpose of testing dental materials and implants, and for the purpose of analyzing food samples.

2. Discussion of the Background

In dentistry there has been a need to measure the forces that are transmitted to the bone surrounding dental implants and adjacent teeth, and to test the strength and durability of dental materials and implants in an oral-like environment. In food science there has been a need to measure the transformation of food and other chewable materials in an objective, reproducible manner. Such would require: (a) generation of the same forces and movements as in real mastication, (b) the presence of a fluid having a chemical effect similar to saliva and food mixtures, and (c) temperature fluctuation and aeration same as in oral cavity.

According to U.S. Pat. No. 6,547,172, artificial saliva can be obtained by mixing in one liter of water between 2 and 10 grams of potassium dihydrogen carbonate, between 0.1 and 1.0 gram of potassium chloride, between 0.1 and 1.0 gram of sodium carbonate, between 0.1 and 1.0 gram of pig pancreas alphaamylase and between 0.1 and 1.0 gram of bovine submaxillary gland mucin, further adjusted to a pH between 7 to 8. According to Condon and Ferracane (1996), a food-like slurry can consist of a suspension of ground poppy-seeds.

Former EnduraTEC Systems Corporation of Minnetonka, Minn. has developed a pneumatically driven universal test system for dynamic applications, able to generate variable axial loads upon two contacting denture-like specimens. A similar system using hydraulic actuators has been developed by MTS System Corporation of Eden Prairie, Minn. A modified MTS system with one horizontal and one vertical actuator was described by DeLong & Douglas (1983) who reported that their system can only approximately generate the mastication motion, and also suggested that testing of dental materials and implants should be performed in a controlled, oral-like environment.

Wang et al. (1998) described the use of a commercially available SCARA-type robot to generate the relative motion and forces between a simulated lower jaw mounted on the robot base, and a simulated upper jaw mounted on the robot end-effector. The forces and torques generated at the interface between the moving jaw and the robot end-effector were recorded as electric signals for later analysis. The same signals were also fed into the robot controller to limit the maximum contact forces between the teeth of the two jaws. In addition, the simulated dental system of Wang et al. includes a dental implant equipped with strain gauges which allows the forces transferred to the implant to be measured.

The devices of Becker et al. (U.S. Pat. No. 4,330,276), Raabe et al. (2012) and Cong et al. (2012) employ parallel mechanisms of the Gogh-Stewart type with six independently controlled actuators. Such parallel mechanisms are widely used in flight simulators, in numerically controlled machine tools or for object manipulation, and are known to have the ability to accurately reproduce a prescribed spatial motion of the moving platform by properly programming their actuators. Such parallel mechanisms however are complicated, both in their mechanical design and in their electronic control means.

A dedicated system for measuring the pressure transmitted to the mandibular alveolar ridge of a lower denture and for measuring the force necessary to shear off various types of food specimens was disclosed in U.S. Pat. No. 5,055,041. This device however has no capabilities of mandibular movement during testing, and there is no reference to controlling the humidity and temperature in the denture area to resemble the conditions in the oral cavity of humans or animals.

The device disclosed in U.S. Pat. No. 5,743,732 consists of a commercially-available phantomhead from Frasaco GmbH of Tettnang, Germany completed with two actuators which move the mandible laterally and protrusively. A means of applying an adjustable occlusal force to the moving jaws is also described in the invention, as well as means of measuring this force using load cells or strain gauges. Although not emphasized in the invention description, the presence of the artificial condyles of the phantomhead is essential for the guidance and support of the mandible as it is driven by the two actuators. These two actuators are a crank-coupler mechanism for inducing the laterotrusive motion, and a multiple-lobed frontal cam for inducing the protrusive motion of the mandible. The preferred embodiment of this referred invention appears to be prone to jamming due to the essentially planar crank-coupler mechanism being deflected perpendicularly to its plane by the protrusive motion induced by the cam. Even in a properly designed embodiment i.e. with the pin joints of the crank-coupler actuator replaced with spherical joints, the proposed device does not seem to be capable of reproducing accurately the complex motion of the human mandible, nor of being capable of generating realistic occlusive forces between the mandible and the maxillae.

In general, the above described masticators and chewing apparatuses suffer from either being complicated in design, from lacking portability, or from being unable to reproduce a desired mandibular motion of humans and animals in a controlled, oral-like environment.

SUMMARY OF THE INVENTION

It is the object of the present invention to provide a parallel mechanism masticator and chewing apparatus (apparatus) in which the chewing process inside the mouth of humans or animals is simulated, such that standardized, reproducible studies can be performed on different foods and other chewable materials.

It is another object of the present invention to provide an apparatus for testing the performance, reliability, strength and durability of dental components, materials and implants in a realistically simulated oral-like environment.

Yet it is another object of the present invention to provide a means for measuring the forces and torque loads developed during mastication.

These and other objects are obtained in accordance with the present invention wherein there is provided an apparatus for realistically reproducing the motion and forces between the upper and lower jaws, in an environment similar to the oral cavity of humans or animals.

The apparatus comprises a frame, a stationary platform (equivalent to the maxillae) which is compliantly attached to the frame, and a movable platform (equivalent to the mandible). Upper dentures are attached to the stationary platform, and lower dentures are attached to the movable platform, said movable platform being driven in a mandibular motion against the stationary platform for testing purposes. The mandibular motion is achieved using six ball-jointed rods each having one end attached to the movable platform and the other end attached either to the frame or to rotary cranks which are driven synchronously by a motor via a transmission.

The present invention also includes devices for measuring the forces and torque loads developed during mastication. In addition, the number of motion cycles undertaken by the mandible are counted either mechanically or digitally, such that endurance tests of testing dental materials and implants can be performed, as well as comparisons between various chewable materials as they are transformed through mastication.

In the present invention, the upper and lower dentures may also be enclosed in a chamber in which an oral-like environment is maintained and monitored. Alternatively, the apparatus is inverted and it is operated partially immersed in a mixture of artificial saliva and/or food slurry.

BRIEF DESCRIPTION OF THE DRAWINGS

Further objects of the present invention will become apparent from the following description of the preferred embodiments with reference to the accompanying drawings in which.

DESCRIPTION OF THE PREFERRED EMBODIMENTS

Figure 1:
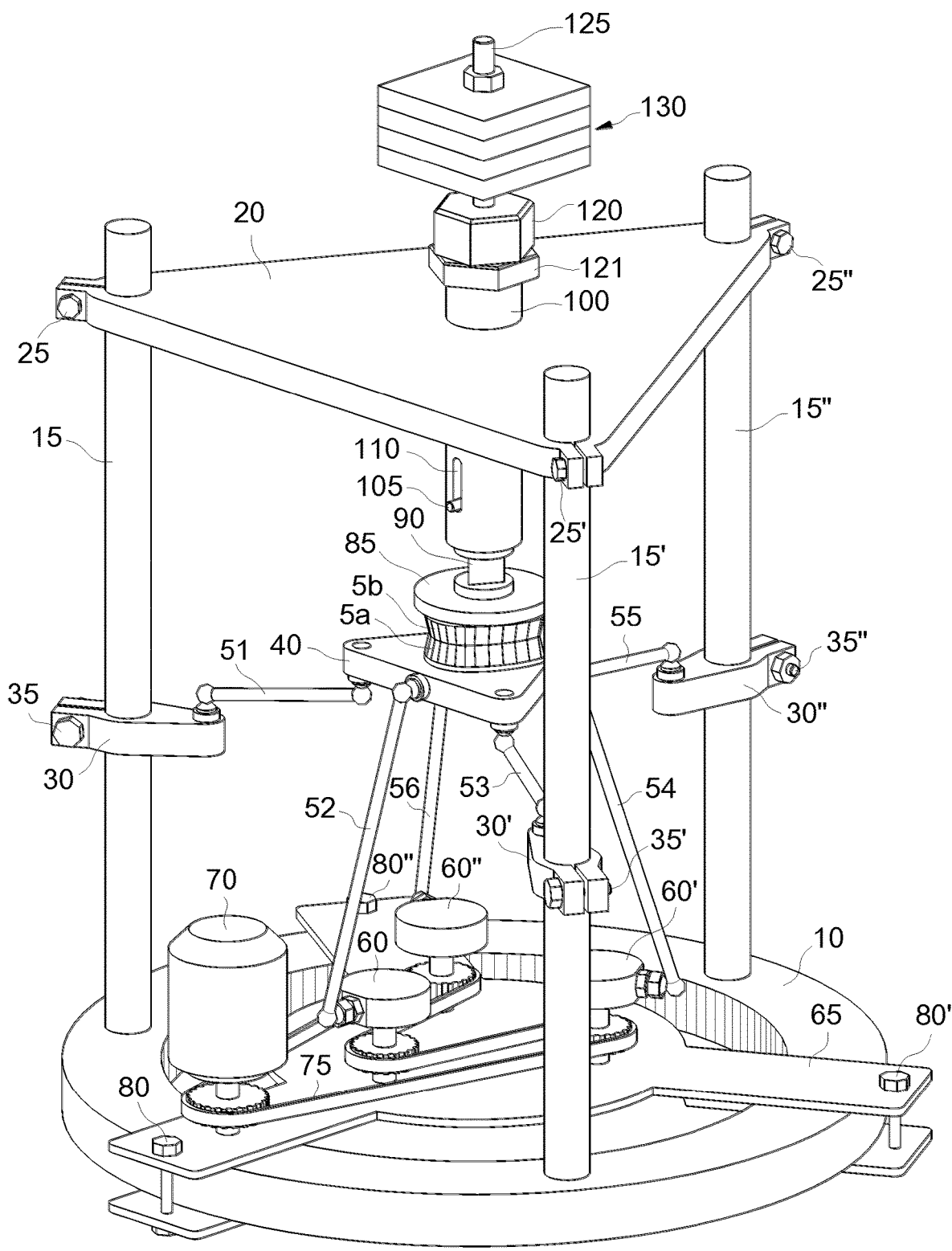
FIG. 1 is a perspective view of the parallel mechanism masticator and chewing apparatus of the present invention.
Figure 2:
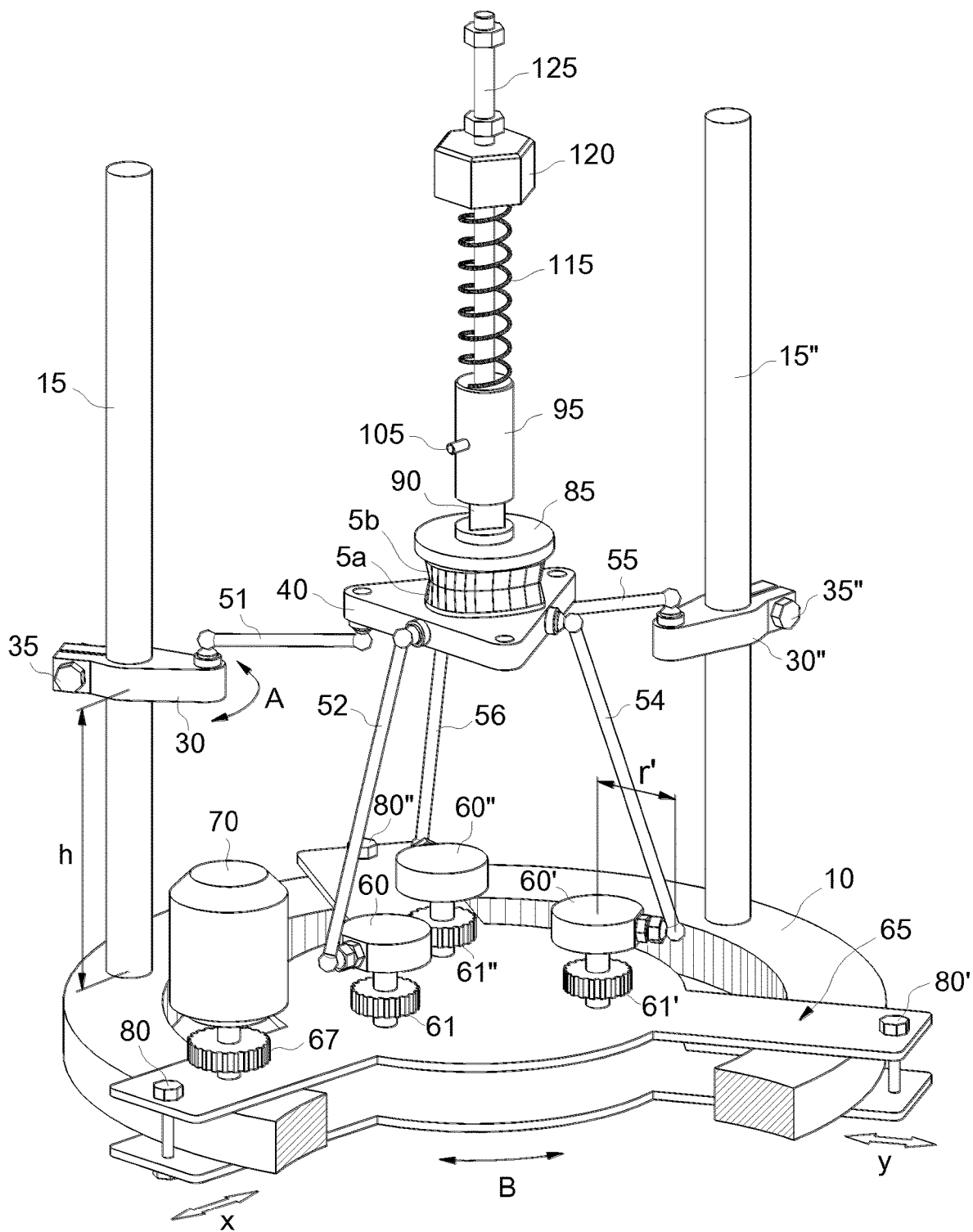
FIG. 2 is a perspective view of the parallel mechanism masticator and chewing apparatus of the present invention depicted with a sectioned base and having some components removed for clarity, and showing some linear and angular adjustabilities of the apparatus.

With reference to FIGS. 1 and 2, parallel mechanism masticator and chewing apparatus (apparatus) of the present invention includes a ring-shaped base 10 upon which three columns 15, 15' and 15" are attached. The upper ends of said columns are stiffened together by a top plate 20, the height of which can be adjusted by the means of screws 25, 25' and 25".

Apparatus also includes brackets 30, 30' and 30" mounted each along columns 15, 15' and 15", the elevation h, h' and h" (h' and h" not shown) and angular orientation A, A' and A" (A' and A" not shown) of said brackets being adjustable by the means of screws 35, 35' and 35".

Apparatus further includes a moving platform 40 which is supported by six ball-jointed rods 51, 52, 53, 54, 55 and 56, of which 51, 53 and 55 are passive rods and 52, 54 and 56 are driving rods.

Apparatus also includes rotary cranks 60, 60' and 60" mounted on a carrier 65 which is clamped onto the ring-shaped base 10 at positions x and y, and orientation B by means of screws 80, 80' and 80". Rotary cranks 60, 60' and 60" are assembled coaxially with driven sprockets 61, 61' and 61", said sprockets having identical number of teeth, and being driven via a chain or a dual-sided timing-belt 75 from a driving sprocket 67 mounted on the shaft of motor 70. The phase angle of rotary cranks 60, 60' and 60" can be modified by holding the shaft of motor 70 fixed, and engaging different teeth of driven sprockets 61, 61' and 61" with the chain or timing belt 75. The radii r, r' and r" (r and r" not shown) of said rotary cranks are adjustable by using threaded means and/or stacked washers known to a person of ordinary skill in the art.

In another embodiment of the invention, sprockets 61, 61', 61" and 67 are configured as spur gears which mesh 67 with 61", 60 with 60' and 60 with 60". In this embodiment, the phase angle of rotary cranks 60, 60' and 60" are modifiable by changing the mating teeth while holding the driving sprocket 67 fix.

The ends of rods 51, 52, 53, 54, 55 and 56 are fitted with spherical joints (also known as ball joints or ball-and-socket joints) of the type that allow the length of said rods to be adjusted and then locked fix, similar to tie rods used in automobile steering and known to a person of ordinary skill in the art. Ball-jointed rods 51, 52, 53, 54, 55 and 56 have one of their spherical-joint attached to moving platform 40. Of these, ball-jointed rods (the passive rods) 51, 53 and 55 have their other spherical-joint end attached to brackets 30, 30' and 30", while ball-jointed rods (the driving rods) 52, 54 and 56 have their other spherical-joint ends attached to rotary cranks 60, 60' and 60".

Apparatus also includes a stationary platform 85 attached via a load cell 90 to a plunger 95 which can slide without the possibility of rotation inside of a tubular guide 100. A sliding without rotation of plunger 95 inside tubular guide 100 is ensured by a pin 105 solidly attached to said plunger, said pin being guided along a slot 110 machined on one side of tubular guide 100. Tubular guide 100 is rigidly attached to top plate 20 and houses to the inside a compression spring 115 which rests on the top end of plunger 95. The other end of spring 115 is hold in place by means of a pierced cap 120 which is adjustably attached to the top end of the tubular guide 100. Plunger 95 extends with a coaxial rod 125 which passes through pierced cap 120 and it is fitted at its top end with a stack of weights 130.

Apparatus also includes a pair of dentures or artificial teeth 5a and 5b mounted to the moving platform 40 and to the stationary platform 85 respectively. In a manner known to a person having ordinary skill in the art, load cell 90 is provided with connectors and means (not shown) of recording and displaying as electric signals the forces and moments generated upon dentures 5b.

In another embodiment of the invention, a second load cell is interposed between dentures 5a and moving platform 40, for the purpose of further measuring the forces and moments generated during mastication.

The occlusal force occurring during mastication between dentures 5a and 5b is provided by the compressing spring 115 and by weights 130. Compression spring 115 can be a standard coil spring thus ensuring essentially a linear occlusal force, or can be a nonlinear spring. As known to a person having ordinary skill in the art, generating a nonlinear occlusal force can be achieved by the use of a coil spring of variable pitch and/or variable radius, or by the use of a properly-shaped block of elastomeric material.

The force provided by compression spring 115 can be changed by modifying the axial position of cap 120 relative to the tubular guide 100. For this purpose, an adjustable assembly is provided between tubular guide 100 and cap 120 by the use of threads and of a jam nut 121.

In another embodiment of the invention where coaxial rod 125 and weighs 130 are missing, the occlusal force between dentures 5a and 5b can be generated by a hydraulic or pneumatic fluid supplied by a pump via flexible hoses or pipes, and delivered inside the space provided by plunger 95, tubular guide 100 and cap 120. As becomes obvious to a person with ordinary skill in the art, in this case plunger 95 must be fitted with appropriate gaskets or seals. The fluid pressure generating the occlusal force can be maintained constant or can be adjusted using known electrovalve and control system, including a feedback-control system which may utilize as input the electric signal from load cell 90. Said feedback-control system can also use information about the position of moving platform 40 relative to the stationary platform 85, as well as information about the number of mastication cycles performed from the beginning of the test, said mastication cycles being determined by placing an encoder on the shaft of motor 70 or by other means known to a person having ordinary skill in the art.

Apparatus may include a cup-like enclosure (not shown) mounted on moving platform 40, and placed around dentures 5a and 5b. For the purpose of generating an environment similar to oral cavities of humans or animals, said cup-like enclosure can be provided with a plurality of openings through which preheated artificial saliva and/or food-like slurry are circulated.

In another embodiment of the invention where no cup-like enclosure is employed, the apparatus is operated in an inverted orientation such that carrier 65, motor 70 and rotary cranks 60, 60' and 60' are located in above positions, and the apparatus is partially submerged in a thermoregulated container filled with artificial saliva and/or a-food-like slurry.

To achieve the desired relative motion between dentures 5a and 5b, the following adjustments can be made, either by trial and error or in a numerically conducted optimization process similarly to an approach described by Simionescu (2017):

- adjust the position (x, y) and orientation B of carrier 65 relative to base 10;
- adjust individually the elevations h, h' and h" of brackets 35, 35' and 35";
- adjust individually the angle A, A' and A" of brackets 35, 35' and 35";
- adjust the phase angle of rotary cranks 60, 60' and 60";
- adjust the radiuses r, r' and r" of rotary cranks 60, 60' and 60";
- adjust the lengths of ball-jointed rods 51, 52, 53, 54; 55 and 56.

While preferred embodiments of the invention have been particularly described in the specification and illustrated in the accompanying drawing, it should be understood that the invention is not so limited. Many modifications, equivalents and adaptations of the invention will become apparent with those skilled in the art without departing from the spirit and scope of the invention as defined in the following claims.

What I claim is:

1. A masticator and chewing apparatus comprising:
   a) a parallel mechanism;
   b) a frame of the apparatus;
   c) an upper denture attached to a stationary platform;
   d) a lower denture attached to a moving platform;
   e) one or more rotary cranks configured to be synchronously driven by a motor via a transmission;
   f) three passive ball-jointed rods jointed to the frame of the apparatus; and
   g) three driving ball-jointed rods jointed to the rotary cranks;
   wherein the moving platform is supported and driven in mandibular motion by the ball-jointed rods;
   wherein the phase angle, radii and location of said rotary cranks relative to the frame, the location of the passive-rod ends relative to the frame, and the lengths of the ball-jointed rods are adjustable and are configured to be adjusted such as to simulate a prescribed motion between said dentures.

2. The apparatus recited at claim 1 further comprising a carrier
   wherein the rotary cranks, the transmission and the motor are attached to the carrier, and
   wherein the position and orientation of the rotary cranks with respect to the frame can be adjusted as a group and can be fixed by clamping.

3. The apparatus as recited at claim 1 further comprising:
   three columns and three brackets;
   wherein each of the brackets is mounted along one of the three columns;
   wherein the elevation and angle of said brackets can be adjusted; and
   wherein the brackets are configured to act as adjustable connections to the frame for the ball-jointed ends of said passive rods.

4. The apparatus as recited at claim 1, wherein the ball-joined rods are adjustable in length, and wherein the length of the ball-joined rods are configured to be locked to the desired length.

5. The apparatus as recited at claim 1, wherein said stationary platform is configured to vertically translate relative to the frame of the apparatus against a mechanism capable of generating adjustable resistive force.

6. The apparatus as recited at claim 5 wherein the mechanism capable of generating adjustable resistive force comprise coil springs, or weights, or a combination of coils springs and weights.

7. The apparatus as recited at claim 5 wherein the mechanism capable of generating adjustable resistive force is an elastomeric block.

8. The apparatus as recited at claim 5 wherein the mechanism capable of generating adjustable resistive force is a compressed fluid.

9. The apparatus as recited at claim 1 further comprising one or more mechanisms for measuring force and torque,
   wherein one of said mechanisms for measuring torque and force is mounted between the upper denture and the stationary platform, and/or
   wherein one of said mechanisms for measuring torque and force is mounted between the lower denture and the moving platform.

10. The apparatus as recited at claim 1 further comprising:
    a mixture of various proportions of artificial saliva and food-like slurry replicating an oral-like environment;
    wherein said dentures are immersed completely or partially in the said mixture; and
    wherein the apparatus is disposed in a vertical position in which the upper denture is vertically above the lower denture.

* * * * *